(12) United States Patent
Buckberry (10) Patent No.: US 9,480,455 B2
(45) Date of Patent: Nov. 1, 2016

(54) VASCULAR ACCESS MONITORING DEVICE (75) Inventor: Clive Buckberry, Warwick (GB)

(73) Assignee: Quanta Fluid Solutions, Ltd., Warwickshire (GB)

( * ) Notice: Subject to any disclaimer, the term of this patent is extended or adjusted under 35 U.S.C. 154(b) by 1239 days.

(21) Appl. No.: 13/393,438

(22) PCT Filed: Jun. 18, 2010

(86) PCT No.: PCT/GB2010/001201
§ 371 (c)(1),
(2), (4) Date: Jul. 12, 2012

(87) PCT Pub. No.: WO2010/146371
PCT Pub. Date: Dec. 23, 2010

(65) Prior Publication Data
US 2012/0271161 A1   Oct. 25, 2012

(30) Foreign Application Priority Data
Jun. 18, 2009 (GB) .................. 0910478.7

(51) Int. Cl.
*A61B 8/00* (2006.01)
*A61M 5/50* (2006.01)
*A61B 7/04* (2006.01)
*A61B 8/08* (2006.01)
*A61M 1/36* (2006.01)
*A61B 5/00* (2006.01)
*A61B 5/02* (2006.01)
*A61B 8/06* (2006.01)
*A61M 5/168* (2006.01)

(52) U.S. Cl.
CPC ............. *A61B 7/04* (2013.01); *A61B 8/0833* (2013.01); *A61B 8/0841* (2013.01); *A61B 8/4227* (2013.01); *A61M 1/3653* (2013.01); *A61M 1/3656* (2014.02); *A61M 5/16836* (2013.01); *A61B 5/0002* (2013.01); *A61B 5/02042* (2013.01); *A61B 8/06* (2013.01); *A61M 5/16831* (2013.01); *A61M 2205/13* (2013.01); *A61M 2205/3375* (2013.01)

(58) Field of Classification Search
None
See application file for complete search history.

(56) References Cited

U.S. PATENT DOCUMENTS

| | | |
|---|---|---|
| 3,921,622 A | 11/1975 | Cole |
| 3,972,320 A | 8/1976 | Kalman |
| 4,205,686 A | 6/1980 | Harris et al. |
| 4,534,756 A | 8/1985 | Nelson |
| 4,648,869 A | 3/1987 | Bobo, Jr. |
| 4,710,163 A | 12/1987 | Butterfield |

(Continued)

FOREIGN PATENT DOCUMENTS

| | | |
|---|---|---|
| DE | 196 09 698 A1 | 9/1997 |
| DE | 19802985 | 7/1999 |

(Continued)

Primary Examiner — Michael Rozanski
(74) Attorney, Agent, or Firm — Hahn Loeser & Parks, LLP (57) ABSTRACT A vascular access monitoring device for monitoring characteristics of a skin piercing vascular access device comprising: an acoustic sensor operable to detect an acoustic emission created by flow through said vascular access device and produce an electrical signal indicative of said emission; electronics processing means for processing and monitoring said electrical signal, and to determine, by identifying a change of characteristic of said signal, the possibility that the vascular access device has become dislodged from its normal working position.

21 Claims, 5 Drawing Sheets (56) References Cited

U.S. PATENT DOCUMENTS

| | | | |
|---|---|---|---|
| 4,771,792 A * | 9/1988 | Seale | 600/587 |
| 5,095,910 A * | 3/1992 | Powers | 600/461 |
| 5,727,550 A | 3/1998 | Montecalvo et al. | |
| 5,882,300 A | 3/1999 | Malinouskas et al. | |
| 6,077,443 A | 6/2000 | Goldau | |
| 6,132,378 A | 10/2000 | Marino | |
| 6,216,029 B1 * | 4/2001 | Paltieli | 600/427 |
| 6,626,832 B1 * | 9/2003 | Paltieli et al. | 600/439 |
| 7,040,142 B2 * | 5/2006 | Burbank | 73/40 |
| 7,874,999 B2 * | 1/2011 | Busby | 604/6.16 |
| 8,114,043 B2 * | 2/2012 | Muller | 604/6.04 |
| 8,137,300 B2 * | 3/2012 | Han et al. | 604/6.09 |
| 8,187,184 B2 * | 5/2012 | Muller et al. | 600/371 |
| 8,192,388 B2 * | 6/2012 | Hogard | 604/6.11 |
| 8,197,431 B2 * | 6/2012 | Bennison | 604/6.06 |
| 8,221,320 B2 * | 7/2012 | Bouton | 600/371 |
| 8,348,850 B2 * | 1/2013 | Frinak et al. | 600/485 |
| 8,360,977 B2 * | 1/2013 | Marttila et al. | 600/371 |
| 8,529,490 B2 * | 9/2013 | Wariar et al. | 604/6.16 |
| 8,535,522 B2 * | 9/2013 | Fulkerson et al. | 210/143 |
| 8,597,505 B2 * | 12/2013 | Fulkerson et al. | 210/86 |
| 8,696,571 B2 * | 4/2014 | Marttila et al. | 600/485 |
| 8,708,908 B2 * | 4/2014 | Bouton | 600/371 |
| 8,708,946 B2 * | 4/2014 | Han et al. | 604/6.09 |
| 8,801,646 B2 * | 8/2014 | Han et al. | 604/5.04 |
| 8,926,544 B2 * | 1/2015 | Hogard | 604/6.11 |
| 8,974,394 B2 * | 3/2015 | Frinak et al. | 600/485 |
| 9,011,334 B2 * | 4/2015 | Bouton | 600/371 |
| 2003/0126910 A1 * | 7/2003 | Burbank | 73/40 |
| 2003/0128125 A1 * | 7/2003 | Burbank et al. | 340/605 |
| 2005/0010118 A1 | 1/2005 | Toyoda et al. | |
| 2005/0038325 A1 | 2/2005 | Moll | |
| 2007/0016053 A1 | 1/2007 | Lo et al. | |
| 2007/0073155 A1 * | 3/2007 | Park et al. | 600/461 |
| 2007/0167808 A1 | 7/2007 | Nozaki | |
| 2008/0108930 A1 * | 5/2008 | Weitzel et al. | 604/5.04 |
| 2008/0195021 A1 * | 8/2008 | Roger et al. | 604/4.01 |
| 2008/0195060 A1 * | 8/2008 | Roger et al. | 604/246 |
| 2008/0221519 A1 | 9/2008 | Schwach et al. | |
| 2008/0275396 A1 * | 11/2008 | Neerken et al. | 604/116 |
| 2009/0082649 A1 | 3/2009 | Muller et al. | |
| 2009/0082676 A1 * | 3/2009 | Bennison | 600/462 |
| 2009/0088683 A1 * | 4/2009 | Roger et al. | 604/65 |
| 2010/0234786 A1 * | 9/2010 | Fulkerson et al. | 604/4.01 |

FOREIGN PATENT DOCUMENTS

| | | |
|---|---|---|
| DE | 198 48 235 C1 | 3/2000 |
| EP | 0 121 931 A2 | 10/1984 |
| EP | 0 232 599 A1 | 8/1987 |
| EP | 0 248 633 A2 | 12/1987 |
| EP | 0 328 163 A2 | 8/1989 |
| EP | 0 330 761 A1 | 9/1989 |
| EP | 0 332 330 A2 | 9/1989 |
| EP | 0 361 793 A2 | 4/1990 |
| EP | 0 895 787 A1 | 2/1999 |
| EP | 1 472 973 A1 | 11/2004 |
| JP | 2005040518 A | 2/2005 |
| WO | WO 91/00113 | 1/1991 |
| WO | WO 97/10013 | 3/1997 |
| WO | WO 99/29356 | 6/1999 |
| WO | WO 2008/100671 A1 | 8/2008 |
| WO | WO 2009/024333 A1 | 2/2009 |
| WO | WO 2009/038834 A1 | 3/2009 |
| WO | WO 2010/089130 A1 | 8/2010 |

* cited by examiner

VASCULAR ACCESS MONITORING DEVICE

CROSS-REFERENCE TO RELATED APPLICATIONS

This application claims priority from PCT/GB/2010/001201 filed on Jun. 18, 2010 and from GB 0910478.7 filed Jun. 18, 2009, which are hereby incorporated by reference in their entireties.

BACKGROUND OF THE INVENTION

1. Field of the Invention

This invention relates to vascular access monitoring, in particular it relates to a device and method for monitoring for the presence of a needle or cannular to determine if it becomes dislodged from a patient.

2. State of the Art

In a number of medical treatment regimes it is necessary to have access to the vascular system through a skin piercing, for example in drug infusion or blood processing treatments like dialysis.

It can be very important to know if a needle becomes dislodged from a patient, and in some cases a dislodged needle can cause serious medical consequences, for example dislodgement of a needle providing life supporting drugs, if not detected could even result in death, as could dislodgement of a blood return needle in a hemodialysis treatment whereby the dialyser can pull blood from the body but not return it. This is especially dangerous in overnight dialysis while the patent is asleep as they would not see the blood escaping.

Several devices have been proposed for detecting if a needle becomes dislodged from a patient, for example in hemodialysis sensors have been used which look at the effect of the presence of a needle on an electric circuit, for example as described in US2005/0038325. Another known device is described in DE 198 02 985 which discloses the use of an optical reflected signal to detect if the needle has become dislodged. The needle has a reflector mounted thereon to reflect an infra red signal from a transmitter back to a receiver. In this device the adaptation of the needle is required which is highly undesirable as it requires a change to a cheap part which is an accepted standard part across the industry.

SUMMARY OF THE INVENTION

It is the purpose of the present invention to provide an alternative to the known sensors that can be used with a standard needle or cannular.

According to a first aspect of the invention there is provided a vascular access monitoring device for monitoring characteristics of a skin piercing vascular access device comprising:

an acoustic sensor operable to detect an acoustic emission created by flow through said vascular access device and produce an electrical signal indicative of said emission; electronics processing means for processing and monitoring said electrical signal, and to determine, by identifying a change of characteristic of said signal, the possibility that the vascular access device has become dislodged from its normal working position.

In one preferred arrangement the acoustic sensor is adapted for location on the patient's skin adjacent a vascular access point.

In an alternative preferred arrangement the acoustic sensor is adapted for location on a flow conduit attached to the vascular access device.

In a preferred arrangement the device is adapted to monitor the flow of blood through a vascular access device, the flow of blood generated by an extra corporeal blood pump.

Preferably the electronics processing means comprises an electrical input means for receiving a signal from an extra corporeal blood pump. More preferably the extra corporeal blood pump is arranged for intermittent pumping and the electronics processing means receives a control signal indicative of the pumping cycle of said extra corporeal blood pump. The electronics processing means is preferably phase locked with the pump cycle of the extracorporeal blood pump and wherein said electronics processing means compares the acoustic signals in either the amplitude or frequency domain, on successive cycles of the extracorporeal pump as it induces flow through said vascular access device.

Preferably the device further monitors background noise and wherein the electronics processing means subtracts the background noise from the signal indicative of the acoustic emissions. Preferably the background noise includes noise created by a patient's heartbeat.

In a preferred arrangement the device monitors background noise in between pump cycles of the extracorporeal blood pump.

In one preferred arrangement the device comprises a second acoustic sensor located on the patients body, remote from said vascular access device, for measuring background noise. In an alternative preferred arrangement a single acoustic sensor is used for creating a signal indicative of acoustic noise due to flow through the vascular access device and indicative of background noise.

As the background noise has its own characteristic pulse, at a rate equal to that of the heartbeat, and has its own range of broadband frequencies, substantially below 5 KHz, it can easily be identified and electronically separated from the total signal received via the sensor monitoring the presence of the vascular access device which will be a combination of the background noise and the nose related to flow through the vascular access device, the nose related to flow through the vascular access device having its own characteristic pulse at a frequency fixed by the blood pump which itself.

Preferably the monitoring device further comprises a second monitoring device for monitoring the presence of the skin piercing vascular access device, the second monitoring device comprising:

a mount having an ultrasonic transmitter and an ultrasonic receiver therein; attachment means for attaching the mount to a patient adjacent a vascular access point such that, in use, a vascular access device entering the patient at the vascular access point, passes underneath a sensing section of the base;

control electronics to monitor the signal received at the receiver, and wherein when the vascular access device is underneath said sensing section, ultrasound produced by said transmitter passes through the patient skin and is reflected by the patients body tissues and by the vascular access device, and when the vascular access device is not underneath said sensing section, ultrasound produced by said transmitter passes through the patients skin and is reflected by the patients body tissue only, and wherein the control electronics detects the presence of a vascular access device by performing a comparison on the received ultrasonic signal.

Preferably the transmitter of the second monitoring device periodically emits an ultrasonic pulse and the receiver receives a reflected ultrasonic pulse.

Preferably the control electronics monitor the received signal from the receiver of the second monitoring device received within in a particular time window, that time window being based on a maximum and minimum expected time of flight of the ultrasonic pulse from the transmitter, to the needle and back to the receiver. Preferably the time window exceeds the expected window by a factor relating to a margin of error.

Preferably the sensor of the second monitoring device is configured to identify ultrasonic reflections from first and second surfaces, one of which is the vascular access device, and the sensor detects a change in the received signals.

Preferably the vascular access device is located beneath the sensing section of the second monitoring device, the reflected signal shows altered characteristics. More preferably, by comparing subsequent received signals received from the receiver of the second monitoring device, a change in either amplitude or frequency content of the received signal can be identified by the control electronics and a warning can be raised that the vascular access device has become dislodged. Alternatively, by comparing the received signal to the transmitted signal, characteristics of the received signal can be identified by the control electronics of the second monitoring device and a warning can be raised when the vascular access device becomes dislodged. As a further alternative, by comparing the received signal from the receiver of the second monitoring device to a model received signal, characteristics of the received signal can be identified by the control electronics of the second monitoring device and if they deviate from the model signal more than a prescribed amount, a warning can be raised that the vascular access device has become dislodged.

Preferably the amplitude, or frequency, of at least a part of the reflected signal received by the receiver of the second monitoring device, changes dependant on the presence of the vascular access device.

Preferably the device further comprises an ultrasonic coupling means for, in use, ultrasonically coupling the second monitoring device to a patients skin.

Preferably the device further comprises means for connection to a medical apparatus.

Preferably, when dislodgement of the vascular access device is sensed, he control electronics sends a signal indicative of that to a medical apparatus, the signal forming a part of the control algorithm for the medical apparatus.

Preferably the control electronics are configured to periodically receive an interrogation from a medical apparatus to perform a self diagnosis check, to carry out a self diagnosis check and to send a signal to the medical apparatus indicative that the diagnosis check was successful and the device is working properly.

The invention will now be described, by way of example, with reference to the following drawings.

DETAILED DESCRIPTION OF THE PREFERRED EMBODIMENTS

Figure 1:
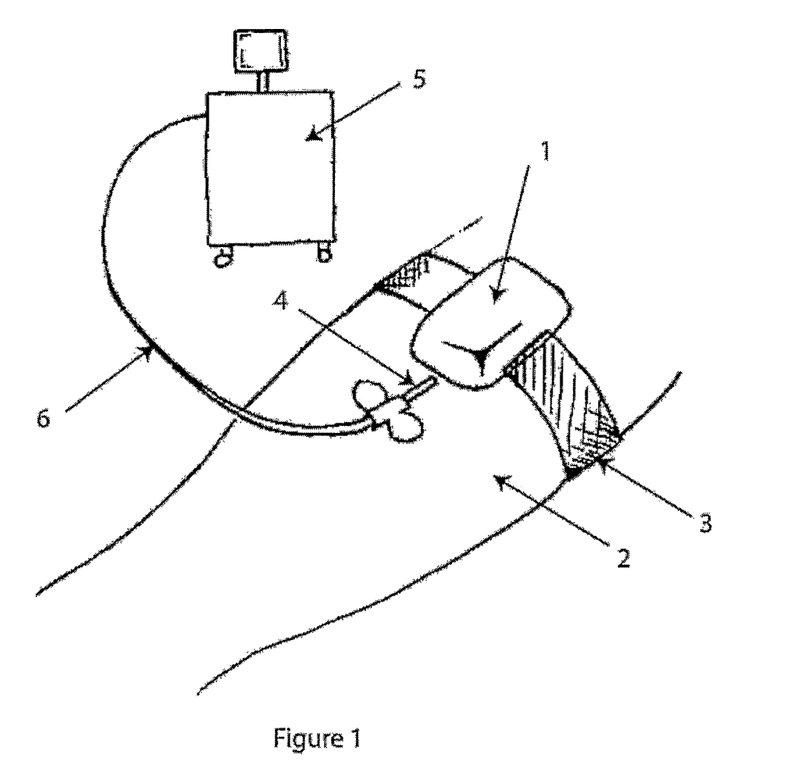
FIG. 1 is a perspective view of one embodiment of the device in use.
Figure 2:
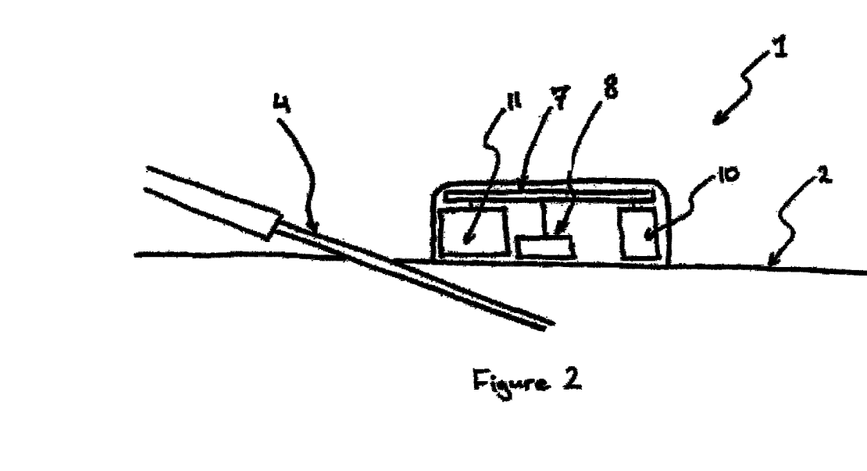
FIG. 2 is a cross section through same embodiment of the device in use.

Referring to FIGS. 1 and 2 the device 1 is shown attached to a patient's arm 2 by means of an attachment strap 3. The device 1 is located adjacent the entry point of a needle 4 which is connected to a medical apparatus 5 by means of a conduit 6. The medical apparatus 5 can be used to either add fluid to or remove fluid from the patient via the needle 4.

Referring to FIG. 2 a cross section through the device in use is shown. The device 1 is positioned adjacent a patients arm. In use an acoustic sensor 8 picks up acoustic signals generated by the flow of fluid through the needle 4 and also background noise generated, at least in part, by the flow of blood through he veins of the patient. The acoustic sensor 8 can be any type of sensor commonly used in electronic stethoscopes and functions in a similar manner. The sensor 8 generates an electrical signal indicative of the sensed sound and transmits the signal to control electronics 7.

The control electronics 7 contain filters to filter the received signal to remove the majority of unwanted background noise. This may be done with passive low pass electronic filters or a more complex active filtering may be used.

Where active filtering is required the sensor monitors the background noise and identifies, within the background noise, noise created by the beat of the heart. This noise can then be subtracted from the signal to give a signal representative of flow through the needle. Where the needle 4 is being used to remove or to return blood from or to the patient the flow through the needle 4 will be cyclic dependant on the pump being used. The sensor 8 measures the background noise between cycles of the blood pump and the control electronics 7 subtract the background noise from the signal created during the pump cycle. Optionally the control electronics 7 can constantly monitor the signal. Within the signal they can identify the timing of the sound pulse created by the beat of the heart and the sound pulse created by the cyclic flow driven by the blood pump. In this configuration the control electronics 7 receive a signal from the blood pump identifying when it is cycling enabling the electronics to identify the signal coinciding with the pumping. As the pump cycle and be heartbeat will not be synchronised, and as the sound pulse associated with the pump cycle can easily be identified the remaining sound pulse will be indicative of the heart beat. In the simplest monitoring device 1 these signals are monitored and, as the sensor 8 is adjacent the patients skin above the needle 4, if the needle 4 becomes dislodged then the pulse identified as coming from flow induced by the blood pump will be lost and an alarm can be raised. The alarm can be raised by any one of a number of known techniques, for example an audible alarm or visual alarm may be incorporated into the device 1, or alternatively where a wireless or wired communication is included as described below the alarm may be raised on a separate medical apparatus or a dedicated alarm unit.

In a more complex device, once the signal representative of the flow through the needle 4 has been identified, it can be monitored for changes in amplitude or frequency which may indicate an occlusion or partial occlusion, the occlusion or partial occlusion resulting in a reduced flow through the needle 4 and a corresponding change in signal. In this configuration the device 1 is powered by a battery 11 which is encapsulated within the device 1. The battery may be recharged by an inductive recharger. In this way the battery can be recharged without needing to open the device to remove the battery. Furthermore, as the device is totally encapsulated it is easy to clean and/or sanitise between uses.

The device 1 further comprises a wireless communications module 10 by which the device can wirelessly communication with the control system of a medical apparatus. In this manner it can receive the signals from the blood pump such that it can perform the identification and separation of noise associated with flow through the needle 4 and background noise described above. Furthermore, in this way, if the needle 4 becomes dislodged from the patient, the device 1 senses it and sends a signal to the medical apparatus 5 to which the needle 4 is connected. The apparatus 5 can then take appropriate action, for example it may sound a warning and/or may stop the medical process using the needle 4. For example, if the needle 4 is being used to remove blood from the patient then if the needle 4 becomes dislodged then the medical apparatus can sound a warning to alert a nurse and can also stop the medical process.

Figure 3:
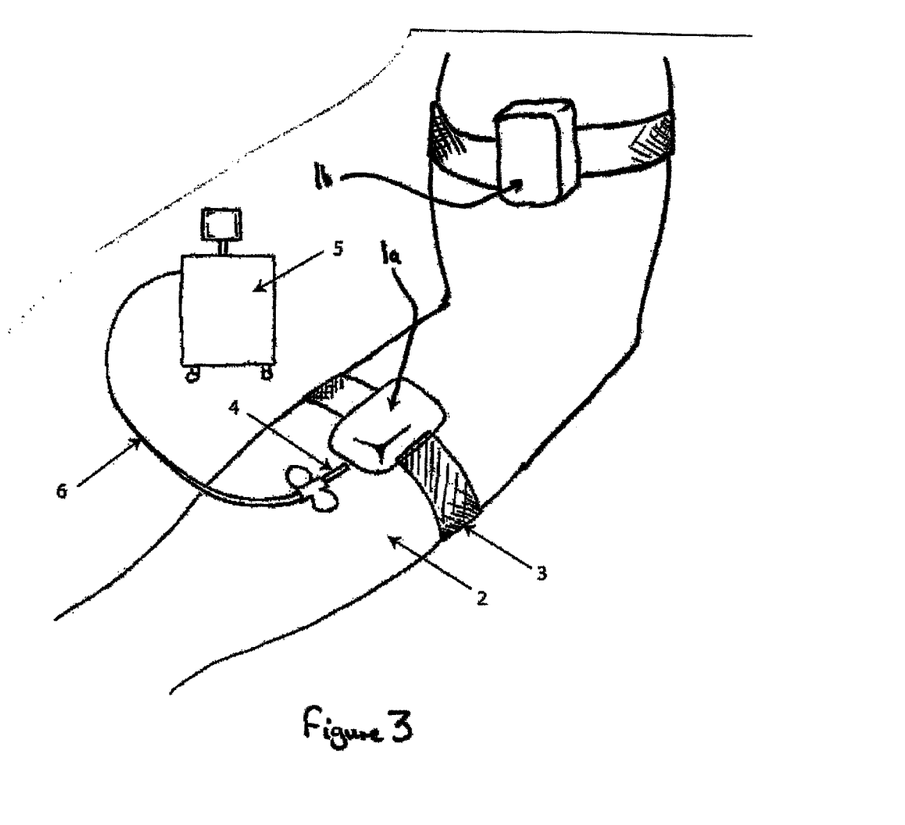
FIG. 3 is a perspective view of an alternative embodiment of the device having two acoustic sensors.

Referring to FIG. 3 an alternative arrangement of a device according to the invention is shown. In this arrangement two devices 1a, 1b are used. Device 1a is positioned on the patients arm adjacent the vascular access point 12 and sensor 1b is positioned adjacent the patients arm at a position discreet from the vascular access point. Both devices are substantially as described with reference to FIG. 2, except in so far as they communicate wirelessly with one another so that the signals can be processed together. In addition wireless communication between the sensors can be used periodically or constantly to ensure that the system is functioning correctly. In this arrangement the signal generated by device 1a will contain two signals superimposed on top of one another, the signal representative of sound caused by the flow of fluid through the needle, and the signal representative of background noise including that associated with heartbeat. The signal generated by device 1b will contain the signal representative of background noise. The signal from device 1b is communicated to the control electronics of device 1a by wireless communication means. By subtracting one signal from the other a clean signal representative of the noise created by flow through the needle 4 can be achieved. This signal can then be monitored for any changes in amplitude, frequency or frequency distribution that may indicate that the needle 4 has become dislodged from its position, or that the flow path from the needle 4 has become at least partially occluded. In this arrangement as a cleaned signal is being monitored for changes it is not necessary for the control electronics of the sensor to receive data from the pump. Depending on the characteristic of the signal being monitored, the control electronics 7 may perform functions commonly used in the field of signal processing, for example Fourier transforms, to the signal to best isolate and identify changes. Such signal processing is common to those skilled in the art of signal electronics.

Figure 4:
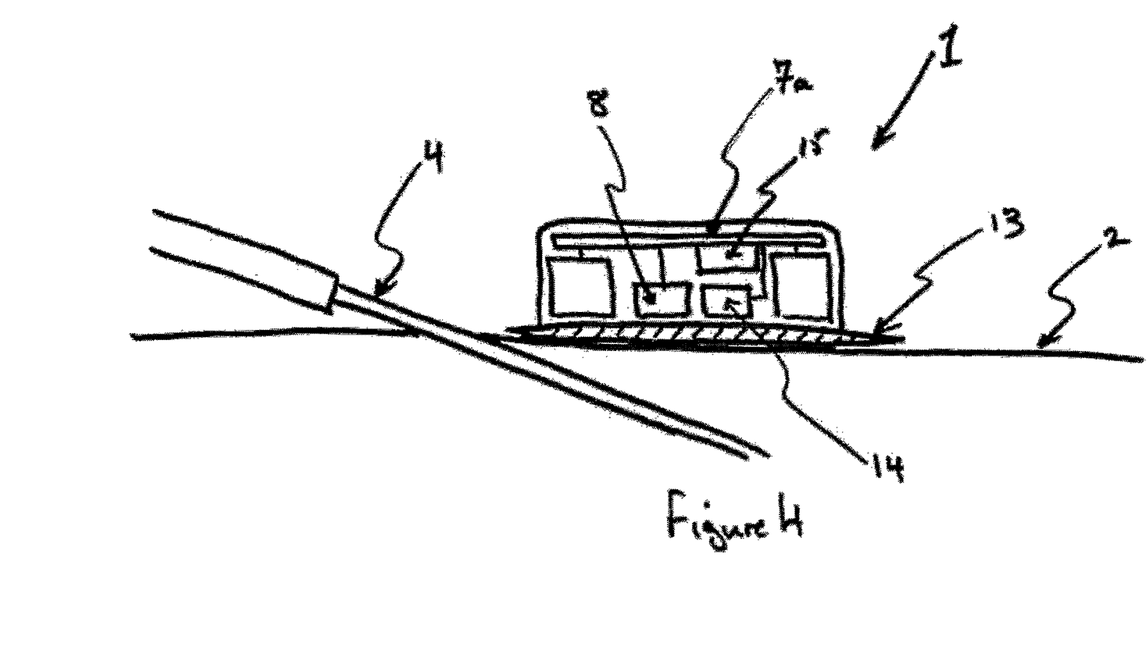
FIG. 4 is a cross section of an embodiment of the device also having ultrasonic sensing.

Referring to FIG. 4 an arrangement of the apparatus is shown providing the arrangement described in relation to FIGS. 1 and 2 in combination with an ultrasonic needle monitoring system. By this method having two independent needle monitoring methods the two systems can be verified against one another to confirm the presence or displacement of the needle. In addition to the details described above, the device further includes a thin gel pack 13 which comprises an ultrasonic coupling gel in a thin flexible plastic pouch. The gel pack 13 conforms to the surface of the patient's arm 2 and to the device 1 such that the space between the patients arm 2 and the device 1 is substantially filled with ultrasonic coupling gel. In use an ultrasonic transceiver 14 transmits an ultrasonic pulse through the gel pack and into the patient's arm 2. The gel pack 13 has walls made of a flexible membrane that has a thickness less than one third of the wavelength of the ultrasound transmitted from the device and the composition of the gel is such that it has an optimum transmission frequency substantially that of the transmission frequency of the device. The patient's arm will absorb some of the ultrasonic signal and reflect some of the signal. The transceiver also receives the reflected signal. The transceiver is connected to control electronics 7a which control the transmitter to transmit ultrasound and receive signals indicative of the received reflected signal from the transceiver 14. The control electronics then compare the received signal, either to the transmitted signal or to a model signal stores in storage means 15 connected to the control electronics 7a to detect if it shows characteristics relating to absorption and reflection by the patient's arm 2, or if it also shows characteristics relating to reflection by a needle 4. Signals relating to a needle 4 will be clearly distinguishable from signals relating to just the patients body as a needle 4, in particular a metal needle as is commonly used, will reflect a much greater amount of ultrasound. The acoustic sensor 8, is designed not to receive sound frequencies in the ultrasound spectrum such that the ultrasonic transducer does not interfere with the acoustic needle monitoring.

Figure 5:
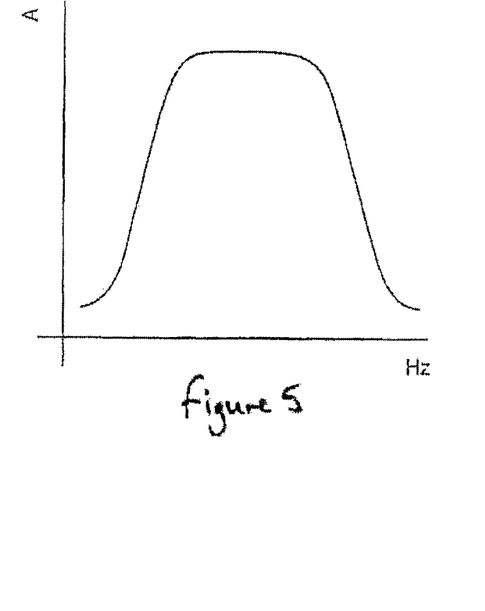
FIGS. 5 and 6 are diagrams of ultrasonic signals.
Figure 6:
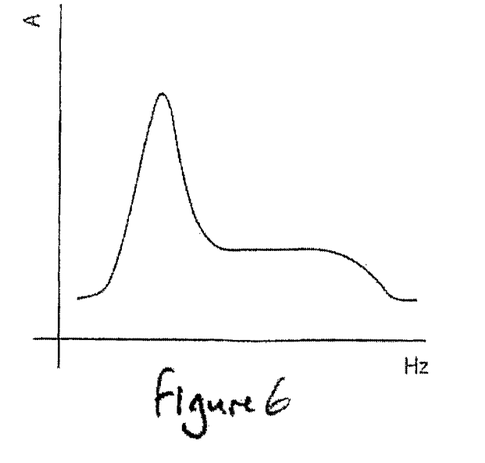

Referring to FIGS. 5 and 6, signal comparisons typical of those use in the device are shown. FIG. 5 shows a typical ultrasonic pulse emitted by the device and FIG. 6 shows two signals, one relating to the reflection of ultrasound by the patients body and the other showing how this changes when a metal needle is present. The control electronics can compare the shape of the received signals and easily identify whether there is a needle present or not.

Other embodiments will be obvious to the person skilled in the art and are included in this invention, for example, the wireless connection could be replaced with a wires connection and the battery could be replaced with a connection to a remote power source.

The invention claimed is:

1. A vascular access monitoring device fbr monitoring characteristics of a skin piercing vascular access device, the monitoring device comprising:
   an acoustic sensor operable to detect an acoustic emission created by flow through said vascular access device and produce an electrical signal indicative of said emission; and
   an electronic monitor that monitors said electrical signal and processes it to determine, by identifying a change of characteristic of said signal, the possibility that the vascular access device has become dislodged from its normal working position;
   wherein the electronic monitor comprises an electrical input that, in use, receives a signal from an extracorporeal blood pump; and
   wherein said extracorporeal blood pump is arranged for intermittent pumping and the electronic monitor receives a signal indicative of a pumping cycle of said extracorporeal blood pump.

2. The monitoring device according to claim 1, wherein:
   the electronic monitor is phase locked with the pumping cycle of the extracorporeal blood pump and wherein said electronic monitor compares the electrical signals on successive cycles of the extracorporeal pump as it induces flow through said vascular access device.

3. The monitoring device according to claim 1 wherein:
   the electronic monitor monitors background noise and subtracts the background noise from the signal indicative of the acoustic emission.

4. The monitoring device according to claim 3, wherein:
   the background noise includes noise created by a patient's heartbeat.

5. The monitoring device according to claim 4, further comprising: a second acoustic sensor located on a patient's body, remote from said vascular access device, for measuring the background noise.

6. The monitoring device according to claim 1, wherein:
the monitoring device monitors background noise in between pumping cycles of the extracorporeal blood pump.

7. The monitoring device according to claim 6, wherein:
the acoustic sensor comprises a single acoustic sensor that is used for creating a signal indicative of acoustic noise due to flow through the vascular access device and indicative of the background noise.

8. The monitoring device according to claim 1, further comprising:
a second monitoring device for monitoring presence of the skin piercing vascular access device, the second monitoring device including:
a mount having an ultrasonic transmitter and an ultrasonic receiver therein,
attachment means for attaching the mount to a patient adjacent a vascular access point such that, in use, the vascular access device entering a patient at the vascular access point, passes underneath a sensing section of the mount, and
control electronics to monitor an ultrasonic signal received at the receiver;
wherein when the vascular access device is underneath said sensing section, ultrasound produced by said transmitter passes through a patient's skin and is reflected by a patient's body tissues and by the vascular access device, and when the vascular access device is not underneath said sensing section, ultrasound produced by said transmitter passes through a patient's skin and is reflected by a patient's body tissue only, and
wherein the control electronics detect, the presence of a vascular access device by performing a comparison on the received ultrasonic signal.

9. The device according to claim 8, wherein:
the transmitter of the second monitoring device periodically emits an ultrasonic pulse and the receiver receives a reflected ultrasonic pulse.

10. The device according to claim 8, wherein:
the control electronics monitor the received signal from the receiver of the second monitoring device received within in a particular time window, that time window being based on a maximum and minimum expected time of flight of an ultrasonic pulse from the transmitter, to the vascular access device and back to the receiver.

11. The device according to claim 10, wherein:
the time window exceeds an expected window by a factor relating to a margin of error.

12. The device according to claim 8, wherein:
the control electronics of the second monitoring device are configured to identify ultrasonic reflections from first and second surfaces, one of which is the vascular access device, and the control electronics detect a change in the received signal.

13. The device according to claim 8, wherein:
when the vascular access device is located beneath the sensing section of the second monitoring device, the received signal shows altered characteristics.

14. The device according to claim 13, wherein:
by comparing subsequent received signals received from the receiver of the second monitoring device, a change in the received signal can be identified by the control electronics and a warning can be raised that the vascular access device has become dislodged.

15. The device according to claim 13, wherein:
by comparing the received signal to a transmitted signal, characteristics of the received signal can be identified by the control electronics of the second monitoring device and a warning can he raised when the vascular access device becomes dislodged.

16. The device according to claim 13, wherein:
by comparing the received signal from the receiver of the second monitoring device to a model received signal, characteristics of the received signal can be identified by the control electronics of the second monitoring device and if they deviate from the model signal more than a prescribed amount, a warning can be raised that the vascular access device has become dislodged.

17. The device according to claim 8, wherein:
an amplitude of at least a part of the received signal received by the receiver of the second monitoring device changes dependent on the presence of the vascular access device.

18. The device according to claim 8, further comprising:
an ultrasonic coupling means configured for, in use, ultrasonically coupling the second monitoring device to a patient's skin.

19. The device according to claim 8, further comprising:
means for connection to a medical apparatus.

20. The device according to claim 19, wherein:
when dislodgement of the vascular access device is sensed, the control electronics send a control signal indicative of that to the medical apparatus, the control signal forming a part of a control algorithm for the medical apparatus.

21. The device according to claim 19, wherein:
the control electronics are configured to periodically receive an interrogation from the medical apparatus to perform a self diagnosis check, to carry out a self diagnosis check and to send a confirmation signal to the medical apparatus indicative that the diagnosis check was successful and the second monitoring device is working properly.

* * * * *